United States Patent
Sharma et al.

(10) Patent No.: US 6,428,825 B2
(45) Date of Patent: Aug. 6, 2002

(54) PROCESS FOR THE PREPARATION OF AN HERBAL-THERAPEUTIC PRODUCT EXTRACTED FROM THE PULP OF A SPECIES EUGENIA JAMBOLANA

(75) Inventors: Suman Bala Sharma, Delhi; Pothapragada Suryanarayana Murthy, Noida; Krishan Madhav Prabhu; Afreena Nasir, both of Delhi, all of (IN)

(73) Assignee: Indian Council of Medical Research, New Delhi (IN)

( * ) Notice: Subject to any disclaimer, the term of this patent is extended or adjusted under 35 U.S.C. 154(b) by 0 days.

(21) Appl. No.: 09/776,650

(22) Filed: Feb. 5, 2001

Related U.S. Application Data

(63) Continuation-in-part of application No. PCT/IN00/00052, filed on May 2, 2000.

(30) Foreign Application Priority Data

Jun. 4, 1999 (IN) .......................................... 834/DEL/99
May 1, 2000 (IN) ...................................... 475/DEL/2000

(51) Int. Cl.$^7$ ................................................ A61K 35/78
(52) U.S. Cl. ........................ 424/777; 424/725; 514/866
(58) Field of Search ................................ 424/725, 777; 514/866

(56) References Cited

U.S. PATENT DOCUMENTS 5,496,553 A * 3/1996 Wilson et al.
5,886,029 A    3/1999 Dhaliwal ..................... 514/456
5,972,342 A * 10/1999 Rakoto Ratsimamanga et al.

OTHER PUBLICATIONS

Achrekar, S. et al. "Hypoglycemic Activity of *Eugenia jambolana* and *Ficus bengalensis:* Mechanism of Action" In Vivo, Vol. 5, p. 143–148, (1991).

Kelkar, S.M. et al. "A Simple Two–step Purification of Antidiabetic Compounds from *Eugenia jambolana* Fruit–Pulp: . . . Properties" Phytomedicine, vol. 3, No. 4, pp. 353–59, (1996/97).

KohliOHLI, K.R. et al. "*Eugenia jambolana:* A Plant Drug With Potential Antidiabetic Property (A Review)" J.Sci.Res.Pl.Med., vol. VI, pp. 1–4, (1985).

* cited by examiner

*Primary Examiner*—Christopher R. Tate
(74) *Attorney, Agent, or Firm*—Ladas & Parry

(57) ABSTRACT

The present invention relates to an herbal therapeutic product for controlling diabetes mellitus comprising at least one hypoglycemic compound extracted from the pulp of fruit *Eugenia jambolana*. The process for the preparation of the herbal therapeutic product to control the glucose level, comprises cleaning and drying the fruit of a species of family Eugenia to remove extraneous material from the outermost layer of the said fruit. De-seeding the fruit and soaking the said de-seeded fruit in water under controlled cooled conditions overnight to retain the activity of hypoglycemic compounds in the mixture of water and pulp of de-seeded fruit. It is followed by mixing the mixture to achieve a uniform consistency.

12 Claims, No Drawings

PROCESS FOR THE PREPARATION OF AN HERBAL-THERAPEUTIC PRODUCT EXTRACTED FROM THE PULP OF A SPECIES *EUGENIA JAMBOLANA*

This application is a continuation-in-part of application Ser. No. PCT/IN00/00052, filed May 2, 2000.

BACKGROUND OF THE INVENTION

1. Field of the Invention

The present invention relates to an herbal therapeutic product for controlling diabetes mellitus comprising at least one hypoglycemic compound extracted from the pulp of a fruit from a species of genus Eugenia specifically *Eugenia jambolana* and a process for the preparation of the same.

An embodiment of the invention resides in the various compounds of the product and their mixture having immediate as well as long lasting effects in controlling diabetes mellitus.

Another embodiment of the invention resides in the four active hypoglycemic compounds comprising the product of the subject invention. These four active hypoglycemic compounds individually have varying degrees of hypoglycemic characteristics, however, the combination has been found to be most effective.

Still another embodiment of the invention resides in the discontinuity of such herbal therapeutic product for a predetermined period after controlling the diabetes of the patients as the hypoglycemic compounds of such products are having the property to control the glucose level, for longer durations.

It has been found that the intake of doses can be postponed for 2–3 days after controlling the glucose level because of the long lasting effects of these hypoglycemic compounds.

The source of carbohydrates in the diet has a significant influence on the lipid(fat) metabolism in human being. An amount of sucrose is increased and the quantity of complex carbohydrates is decreased, the concentration of cholesterol and more particularly of triglycerides increases which has a correlation between blood lipid concentration and impaired glucose tolerance.

One of the objects of the present invention is that the product of the present invention is a 100% herbal product without any side effects.

Another object of the present invention is to treat the defect in metabolism of a patient suffering from diabetes, by increasing the activity of the glucose utilizing enzymes in the liver, muscles and adipose tissues.

The present invention relates to the product obtained from the species of genus Eugenia having hypoglycemic effects in the blood sugar level.

2. Description of Related Art

Kelkar in his article XP-000940531, *Phytomedicine*, Volume 3 (4), pages 353–359, 1996/97, teaches a purification of antidiabetic compounds from *Eugenia jambolana* fruit-pulp; proteolytic resistance and other properties.

The compounds have been identified as a peptidylglycan and an oligosaccharide with molecular weights of 6.0 and 1.2 kD, respectively. The binding between the sugars and the peptide in the peptidylglycan appears to be covalent. The amino acid and sugar composition of the peptidylglycan have been determined as having the sugars of the oligosaccharide. The intrinsic color of the peptidylglycan was attributed to the compound itself and not to the presence of pigment or metal. The peptidylglycan was resistant to degradation by proteolytic enzymes in vitro, explaining its efficacy in oral feeding.

Kelkar further teaches separation of hypoglycemic compound by molecular sieving (depending upon the size of two molecular). In short the purification process described Kelkar involves ultrafiltration, gel filtration, paper chromatography and SDS polyacrylamide tube gel electrophoresis.

Kelkar also teaches that hypoglycemic activity was found at two distinct positions eluting at 35–45 ml & 60–75 ml, which is not very precise, since vol. of fractions vary with the amount of loading, width and size of column and height of packed material.

Saigeeta Achrekar et al. in its review article XP000608379 teaches Hypoglycemic Activity of *Eugenia jambolana* and *Ficus bengalensis:*

BRIEF SUMMARY OF THE INVENTION

Accordingly, the present invention relates to a herbal therapeutic product for controlling diabetes mellitus comprising at least one hypoglycemic compound extracted from the pulp of a species of the genus Eugenia, specifically *Eugenia jambolana*.

The process for the preparation of the herbal therapeutic product to control the glucose level, comprises cleaning and drying the fruit of a species of family Eugenia to remove extraneous material from the outermost layer of the said fruit. De-seeding the fruit and soaking the said de-seeded fruit in water under controlled cooled conditions overnight to retain the activity of hypoglycemic compounds in the mixture of water and pulp of de-seeded fruit. It is followed by mixing the mixture to achieve a uniform consistency.

DETAILED DESCRIPTION OF THE INVENTION

The process for the preparation of such herbal product comprising cleaning and drying the fruit of a species of genus Eugenia of family Myrtaceae to remove the extraneous material from the outer layer of the fruit, deseeding the fruit, soaking the de-seeded pulp in water, mixing the mixture of water and pulp and keeping it overnight in a controlled cooled conditions to maintain the activity of hypoglycemic compounds, filtering the mixture in a conventional manner, washing the residue with water to extract all the active compounds from the mixture of water and pulp in the form of clear watery solution, reducing the water content by keeping the clear watery solution in controlled freezing conditions by conventional means to obtain the residues in a concentrated form, purifying the concentrated product in a chromatography by using slurries of different columns, and adding buffers in the purified mixture present in the chromatography to elute the mixture of hypoglycemic compounds.

The various steps involved in the aforementioned process are:

(a) The fruit of *Eugenia jambolana* is cleaned and dried to remove the extraneous material from the outer layer of the fruit;

(b) The seeds are removed from the fruit in a conventional manner and kept separately;

(c) The resulting de-seeded pulp is soaked in (distilled) water and the same is mixed to obtain a uniform consistency of the liquid;

(d) The mixture is kept overnight in a controlled cooled condition preferably between 4–10 degrees centigrade to maintain the activity of the hypoglycemic compounds present in the fruit pulp;

(e) The mixture is filtered in a conventional manner;

(f) The residue is washed with water to extract all active compounds from the pulp in the form of clear watery solution;

(g) The water content of the solution is reduced by keeping the clear watery solution in freezing conditions by conventional means to concentrate the residue;

(h) The concentrated product is purified by treating the same with slurries of solvents selected preferably from diethyl amino ethyl cellulose, anion exchange resins or silica gel and distilled water in the chromatography; and (i) Buffers are added in the purified mixture present in the chromatography to elute the hypoglycemic compounds from the mixture.

The water content from said mixture can be reduced optionally to get the end product in solid form. The water is extracted from the mixture after filtration by means of lypholizer.

The pulp of *Eugenia jambolana*, is subjected to column chromatography for a period of 15 minutes to 2 hours to obtain a hypoglycemic fraction at a slightly acidic pH of 5–7, preferably 6.0 to 6.5.

The hypoglycemic fraction is subjected to thin layer chromatography using silica gel to form at least 2 visible bands. The $R_f$ value of all the four bands is between 0.1–1.0, wherein the $R_f$ value of one visible band which has a highly active hypoglycemic compound is between 0.5 to 0.7 and the $R_f$ value of the less active hypoglycemic compounds is between 0.1–0.2 and 0.9–1.0.

The pH of the column containing the mixture of chemical compounds is maintained at 6.0–8.0, preferably 6.5 to 7.5.

The buffer used in the chromatography is selected preferably from a phosphate buffer or citrate buffer.

The pH of the mixture of hypoglycemic compounds is to be maintained neutral.

The mixture of hypoglycemic compounds were further analyzed to separate the active hypoglycemic compounds by means of thin layer chromatography to separate the different compounds in the form of separate bands. Such bands were further exposed to an iodine chamber for the clear demarcation of the individual compound. It has been found that out of four such hypoglycemic compounds present in the mixture, two compounds have an immediate effect in controlling and maintaining the blood sugar level, while the other two hypoglycemic compounds maintain the effects of the first two compounds.

In the thin layer chromatography, the mixture of hypoglycemic compounds are dropped in the lower most end of a silica gel coated plate to get the deposition of the hypoglycemic compounds in the form of bands on the silica gel coated plate by running with a mixture of solvents for 2–3 hours in the ascending manner. The solvents used are n-butanol, acetic acid and water in the ratio of 5:1:4. The silica gel coated plate with bands of hypoglycemic compounds is dried in cooled conditions and is exposed to an iodine chamber to get the clear demarcation of the different hypoglycemic compounds bands which are extracted from the silica gel coated plate along with the fractions of silica gel. The extracted hypoglycemic compounds along with the silica gel is mixed with water for the separation of the silica gel by centrifugation.

The water used in the subject process is preferably distilled water.

A study was conducted to determine the effects of the herbal therapeutic product prepared from the pulp extracted from the genus Eugenia on the blood glucose, liver, aorta, pancreas and heart. The results were that the product was very effective with no side effects. This is the main embodiment of the present invention.

Various tests were conducted to analyze the effects of the product on testing the blood glucose level in fasting and in glucose tolerance test.

A test was conducted on alloxan induced diabetic rabbits where the product prepared from the process of the present invention was given to the alloxan induced diabetic rabbits after drawing blood from the fasting rabbits. After giving a dose of the product, the blood was drawn again from the rabbits after 90 minutes. After that, 2 grams of glucose in a water solution was given to the same rabbits. The blood was again drawn from the rabbits after two hours of glucose feed. It was found that the mixture reduced the blood glucose level even after the glucose feed, which was due to the rise in insulin level in the blood.

The product was found to increase the activity of enzymes in the liver, muscle and adipose tissue, which use glucose and thereby reduce blood glucose level. The product was further found to reduce the level of lipids in blood which are responsible for heart diseases like total cholesterol, low density lipoprotein cholesterol, very low density lipoprotein cholesterol and triglycerides. At the same time, the product increases the level of favourable lipids for health such as high density lipoprotein cholesterol (HDLC). The mixture of hypoglycemic compounds were found to have no adverse effects on liver and kidney functions.

No abnormalities were found after conducting the histopathology of liver, aorta, pancreas and heart, when the patient was treated with the product of the present invention.

Hence, the present invention relates to a herbal therapeutic product to control the glucose level in diabetes mellitus and also minimizes the risk of heart diseases extracted from the pulp of a species from the genus Eugenia prepared from the process as herein before described, wherein the product comprises the hypoglycemic compound or a group of the hypoglycemic compounds in the form of a product.

EXAMPLES

Example 1

To prepare the herbal therapeutic product of the present invention, 1 Kg of pulp of the fruit from the genus Eugenia is mixed with 500 ml of distilled water and kept overnight in cooled conditions at 4° C., the mixture is then filtered by conventional manner, and the residue is washed twice or thrice to extract all the active compounds from the mixture. The water from the resultant mixture is then reduced by keeping the resultant mixture in a lypholizer to get the residues in paste form, the chromatography of the paste is done using diethyl amino ethyl cellulose. A phosphate buffer is then added to elute the mixture of hypoglycemic compounds. The hypoglycemic compounds were given in the form of solution mixed with water.

Example 2

The herbal therapeutic product of the present invention is prepared by taking 500 grams of pulp of the fruit *Eugenia Jambolana* and mixing it in 200 ml of distilled water, which is kept overnight in cooled conditions at 4–10° C. The mixture is then filtered by a conventional manner and the residue is washed twice to extract all the active compounds from the mixture. The water from the resultant mixture is extracted by keeping the resultant mixture in a lypholizer to get the residues in paste form. The chromatography of the paste is done and a phosphate buffer is then added to elute the mixture of hypoglycemic compounds. The hypoglycemic compounds are dropped in very small quantity on the lower most end of a glass plate having a silica coating on it. The plate is then placed in a glass chamber having solvents n-butanol, acetic acid and water in the ratio of 4:1:5, the bands of hypoglycemic compounds are deposited on the silica coated plate by capillary action. The plate with the deposition of hypoglycemic compounds is removed from the glass chamber and dried in cool conditions. Then, the plate is exposed to an iodine chamber to obtain a clear demarcation of the different hypoglycemic compounds bands which are extracted by scratching them off of the plate in the form of powder along with silica gel abstracts, the same is mixed with water for the separation of said silica gel by centrifugation.

What is claimed is:

1. A process for the preparation of an herbal therapeutic product for controlling blood glucose levels, extracted from pulp of fruit of *Eugenia jambolana,* comprising cleaning and drying the fruit to remove extraneous material from the outer layer of the fruit, deseeding the fruit to form a de-seeded pulp, soaking the de-seeded pulp in water, mixing the water and pulp to form a mixture and keeping it overnight in controlled cooled conditions to maintain activity of hypoglycemic compounds present in the fruit pulp, filtering the mixture to form a residue, washing the residue with water to extract all active compounds in the form of a clear watery solution, reducing water content of the solution to obtain a filtrate in a concentrated form, purifying the filtrate by column chromatography using slurries of different column materials to elute the mixture of hypoglycemic compounds by adding different buffers to form a second mixture, conducting thin layer chromatography of the second mixture to separate the hypoglycemic compounds in the form of bands, exposing the bands in an iodine chamber for clear demarcation of the hypoglycemic compounds and extracting the hypoglycemic compounds to recover the herbal therapeutic product containing said hypoglycemic compounds for controlling blood glucose levels.

2. The process as claimed in claim 1, wherein the mixture of water and pulp is kept overnight at a temperature from 4 to 10° C.

3. The process as claimed in claim 1, wherein the water is reduced by means of a lyophilizer.

4. The process as claimed in claim 1, wherein the slurries are selected from the group consisting of diethyl amino ethyl cellulose and anion exchange resins or mixtures thereof.

5. The process as claimed in claim 1, wherein the buffers are selected from the group consisting of phosphate buffers and citrate buffers or mixtures thereof.

6. The process as claimed in claim 1, wherein the buffers are maintained at a pH in the range of 6.0–8.0.

7. The process as claimed in claim 1, wherein the thin layer chromatography is conducted using a silica gel coated plate wherein the hypoglycemic compounds are applied to the lower most end of a silica gel coated plate to obtain deposition of the hypoglycemic compounds in the form of bands on the silica gel coated plate by running with a mixture of solvents for 2–3 hours in ascending manner.

8. The process as claimed in claim 1, wherein the solvents are n-butanol, acetic acid and water in the ratio of 4:1:5 to 5:1:4.

9. The process as claimed in claim 7, wherein the silica gel coated plate with the bands of the hypoglycemic compounds is dried at cooled temperature.

10. The process as claimed in claim 9, wherein the silica gel coated plate is exposed to iodine in a closed chamber to obtain a clear demarcation of the different bands containing the hypoglycemic compounds and extracting the bands containing the hypoglycemic compounds same from plate.

11. The process as claimed in claim 1, wherein the water is distilled water.

12. A process as claimed in claim 1 wherein the pH is maintained in the range 6.5–7.5.

* * * * *